United States Patent [19]

Nguyen et al.

[11] Patent Number: 5,829,589
[45] Date of Patent: Nov. 3, 1998

[54] PEN NEEDLE MAGAZINE DISPENSER

[75] Inventors: Tuan V. Nguyen, Rockaway; Michael A. Dibiasi, West Milford; Robert E. West, Morristown, all of N.J.; Matthew Murray, Mattapoisett, Mass.; Scott Reed, Monroe, Conn.; William J. Allen, Stratford, Conn.; Jeffrey A. Stein, Woodbridge, Conn.

[73] Assignee: Becton Dickinson and Company, Franklin Lakes, N.J.

[21] Appl. No.: 928,275

[22] Filed: Sep. 12, 1997

[51] Int. Cl.⁶ .................................................... B65D 85/24
[52] U.S. Cl. ............................................ 206/366; 206/443
[58] Field of Search ..................... 206/365, 366, 206/370, 438, 443, 380

[56] References Cited

U.S. PATENT DOCUMENTS

5,224,596  7/1993  Kruger ................................ 206/365 X
5,285,896  2/1994  Salatka et al. ........................... 206/366

Primary Examiner—Jacob K. Ackun
Attorney, Agent, or Firm—Alan W. Fiedler

[57] ABSTRACT

A pen needle magazine dispenser designed to be received and carried in a cap of a medication delivery pen. The dispenser having a cover rotatably mounted on a circular shaped container with a plurality of cavities, wherein each cavity is dimensioned to receive one pen needle. The pen needle being of a type that is forced fit into an adaptor on the pen using threads on the pen needle and corresponding threads in the cavity. The cover includes a slot that is rotated into alignment with one of the cavities in the container to provide the user with access to one unused pen needle and thereby permit the pen needle to be mounted on the pen. After use the used pen needle is returned to the cavity and the cover is rotated until the slot is aligned with another cavity containing the next unused pen needle to be used during the next injection.

15 Claims, 6 Drawing Sheets

PEN NEEDLE MAGAZINE DISPENSER

BACKGROUND OF THE INVENTION

1. Field of the Invention

The subject invention relates to a pen needle dispenser for a new pen needle and, more particularly, to pen needle magazine dispenser that holds and dispenses sterile pen needles for medication delivery pens and that safely stores the needles after use.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber. A needle cannula is mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal. Medication in the prior art vial is accessed by piercing the elastomeric seal with the needle cannula. A selected dose of the medication is drawn into the chamber of the syringe barrel by moving the plunger a selected distance in a proximal direction. The needle cannula is withdrawn from the vial, and the medication is injected into a patient by moving the plunger in a distal direction.

Some medication, such as insulin is self-administered. The typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. A prior art medication delivery pen is identified generally by the numeral 1 in FIG. 1. Pen 1 contains a cartridge with sufficient medication for several doses. The prior art cartridge has opposed proximal and distal ends. The distal end is closed by a pierceable and resealable rubber septum identified by the numeral 2 in FIG. 1. The proximal end receives a stopper in sliding fluid-tight engagement. The prior art cartridge is disposed in an elongate pen-like body 4 with a proximal end (not shown) and an opposed distal end 6. The proximal end of the pen body includes a plunger for selectively driving the stopper of the cartridge in the distal direction and a dose setting mechanism for determining the distance through which the plunger and stopper can move. Distal end 6 of pen body 4 includes an array of threads 8 for threaded engagement with a pen needle assembly 90. Pen needle assembly 90 includes a needle cannula 91 with opposed proximal and distal points 92 and 93 and a threaded mounting skirt 94 which surrounds the proximal tip 92. Mounting skirt 94 is threadably engageable with threads 8 on distal end 6 of pen body 4. A safety shield 95 is releasably engaged over distal point 93 and portions of mounting skirt 94 to prevent accidental needle sticks.

Figure 1:
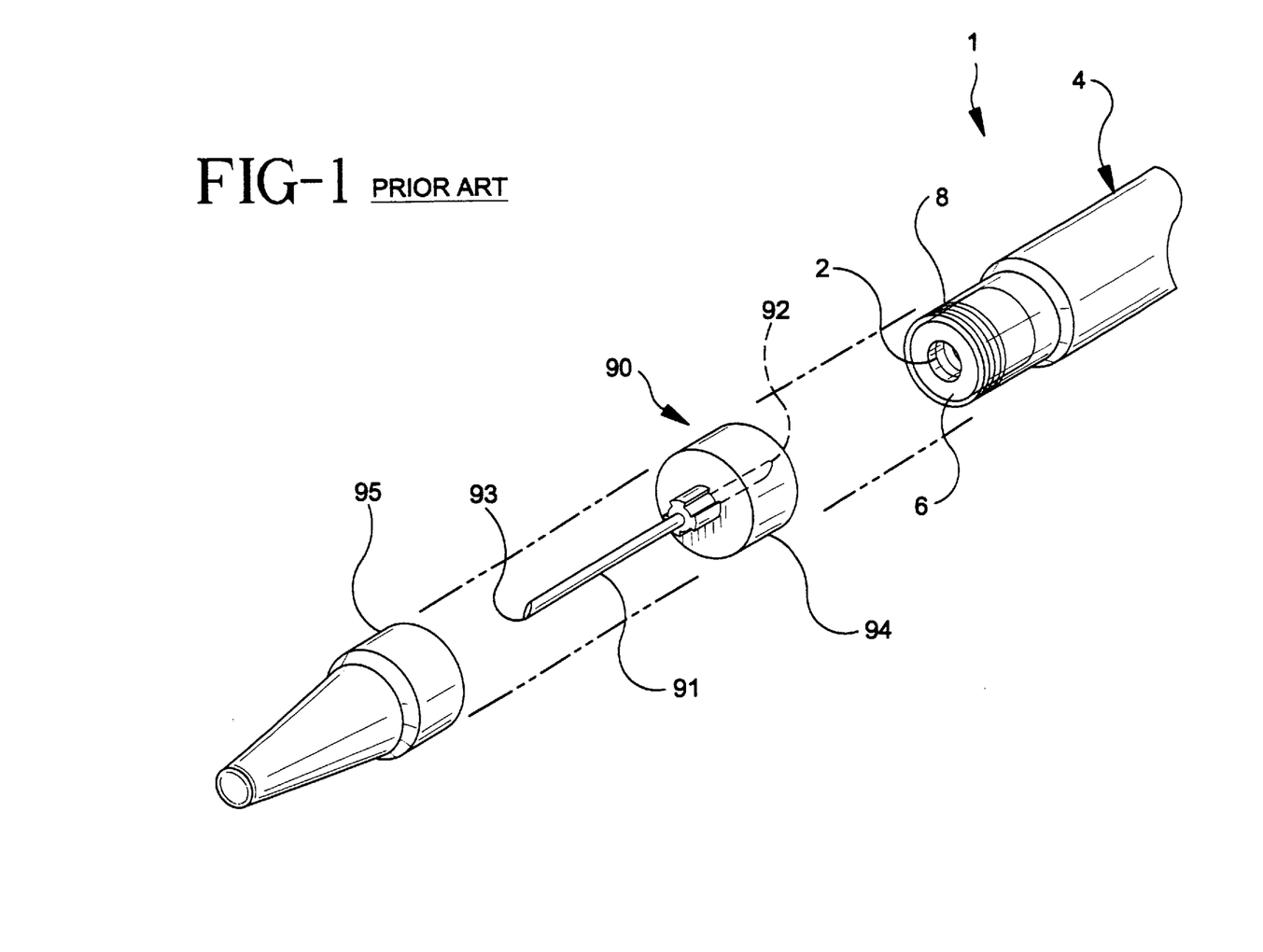
FIG. 1 is an exploded perspective view of a prior art pen needle and the distal end of a prior art medication delivery pen with which the present invention is intended to be used.

A person who must periodically inject doses of medication will carry a medication delivery pen 1 and a supply of pen needle assemblies 90. Each pen needle assembly 90 has its needle cannula 91 safely and sterility sealed in its own shield 95, and is accessed immediately prior to administering a dose of medication. Pen needle assembly 90 then is mounted to distal end 6 of prior art pen 1. This mounting causes proximal point 92 of needle cannula 91 to pierce rubber septum 2 of the cartridge, to place needle cannula 91 in communication with the medication in pen 1. Pen 1 then is used to inject the selected dose of medication. After completing the injection, needle assembly 90 is separated from pen 1 and is discarded. Pen 1 may be used repeatedly in this manner until the medication is exhausted. Such prior art pens offer many conveniences and efficiencies. However, the storage of unused needles and the final disposal of used needles has presented problems. In particular, supplies of new needles often are loosely scattered in the bottom of purses or briefcases, and used needles are often disposed of unsafely.

SUMMARY OF THE INVENTION

The subject invention relates to a storing and dispensing apparatus for needle assemblies used with hypodermic syringes and preferably a new type of pen needle that is designed to attach to an adaptor having conventional threads that mate with threads 8 on medication delivery pens.

The pen needle dispenser of the present invention includes a magazine dispenser having a cover rotatably mounted on a container with a plurality of cavities, with each cavity dimensioned to receive a new type of pen needle assembly. The cover includes a slot that is rotated into alignment with a cavity in the container that contains an unused pen needle. When the slot is aligned with such a cavity, the user inserts the adaptor on the medication delivery pen into the cavity and rotates the pen to mount the unused pen needle on the medication delivery pen. After the injection has been performed, the used pen needle is returned to the cavity by inserting the used pen needle in the cavity and rotating the pen to detach the pen needle from the adaptor on the pen. The user then rotates the cover until the slot in the cover provides access to the next cavity containing another unused pen needle to be used during the next injection.

An object of the present invention is to prevent the pen needle from being reused by having it covered in the pen needle magazine dispenser. In addition, once the cover has been rotated to the next cavity, the pen needle magazine dispenser provides means to prevent the cover from rotating back to used pen needles.

Another object of the present invention is to provide a user with a convenient way to carry, dispose of and keep track of their personal pen needle usage. The pen needle magazine dispenser is designed to fit in the cap of the medication delivery pen and contain a predetermined number of pen needles in respective cavities, with each cavity being sealed by a numbered label or sterility membrane. The numbered labels indicate how many unused pen needles remain in the pen needle magazine dispenser.

Another object of the present invention is to provide an adaptor that is threaded onto the distal end of conventional medication delivery pens so that a new type of pen needle can be used with such conventional medication delivery pens. The new type of pen needle includes a base having threads on one end that drive the other end of the base into the adaptor to create a friction fit between the adaptor and the base. The driving force is generated by using the adaptor to rotate the pen needle relative to its cavity and thereby unthread the pen needle from the cavity and force fit it in to the adaptor.

These and other aspects, features and advantages of the present invention will become apparent from the following detailed description taken in conjunction with the accompanying drawings.

DETAILED DESCRIPTION

Figure 2:
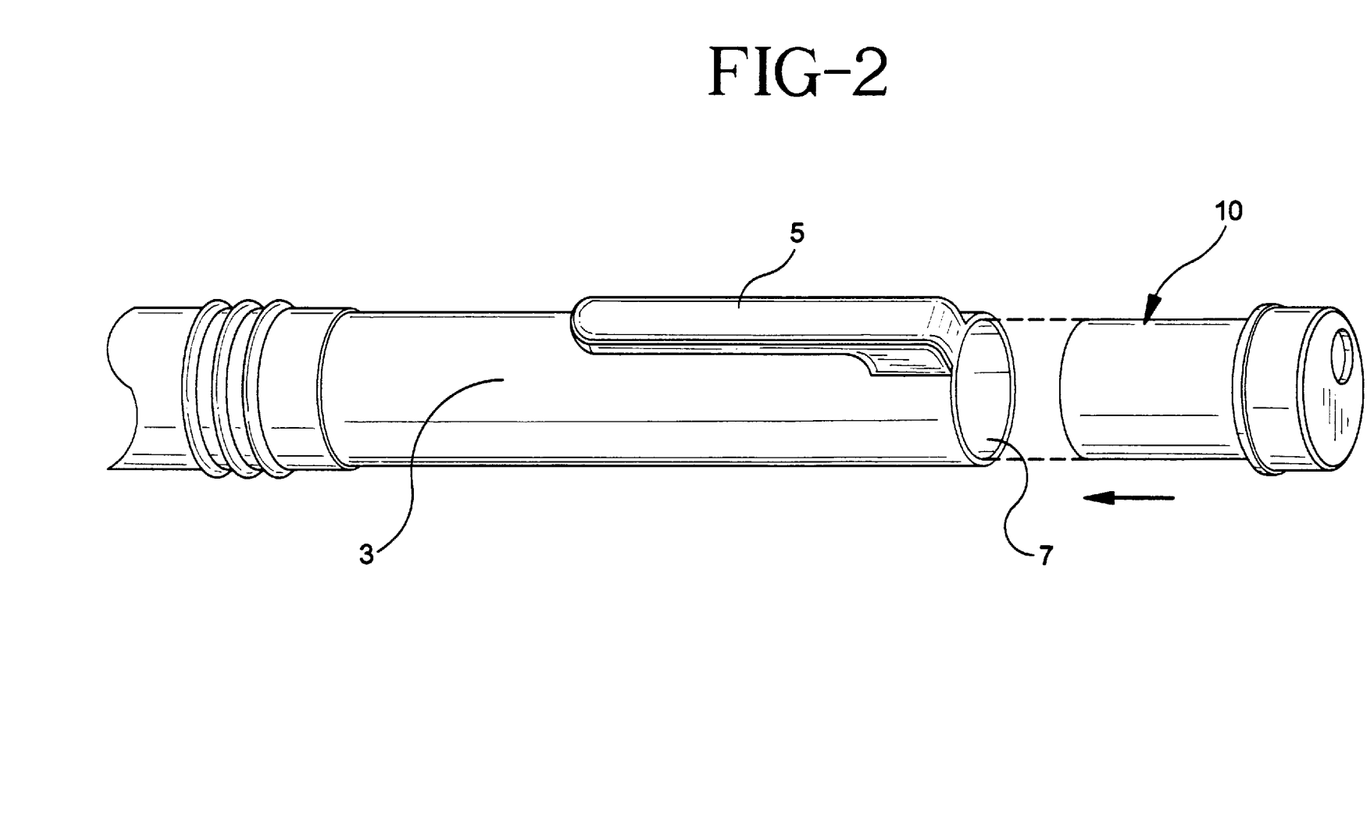
FIG. 2 is an exploded perspective view of a cap on a medication delivery pen and a pen needle magazine dispenser according to the present invention.
Figure 3:
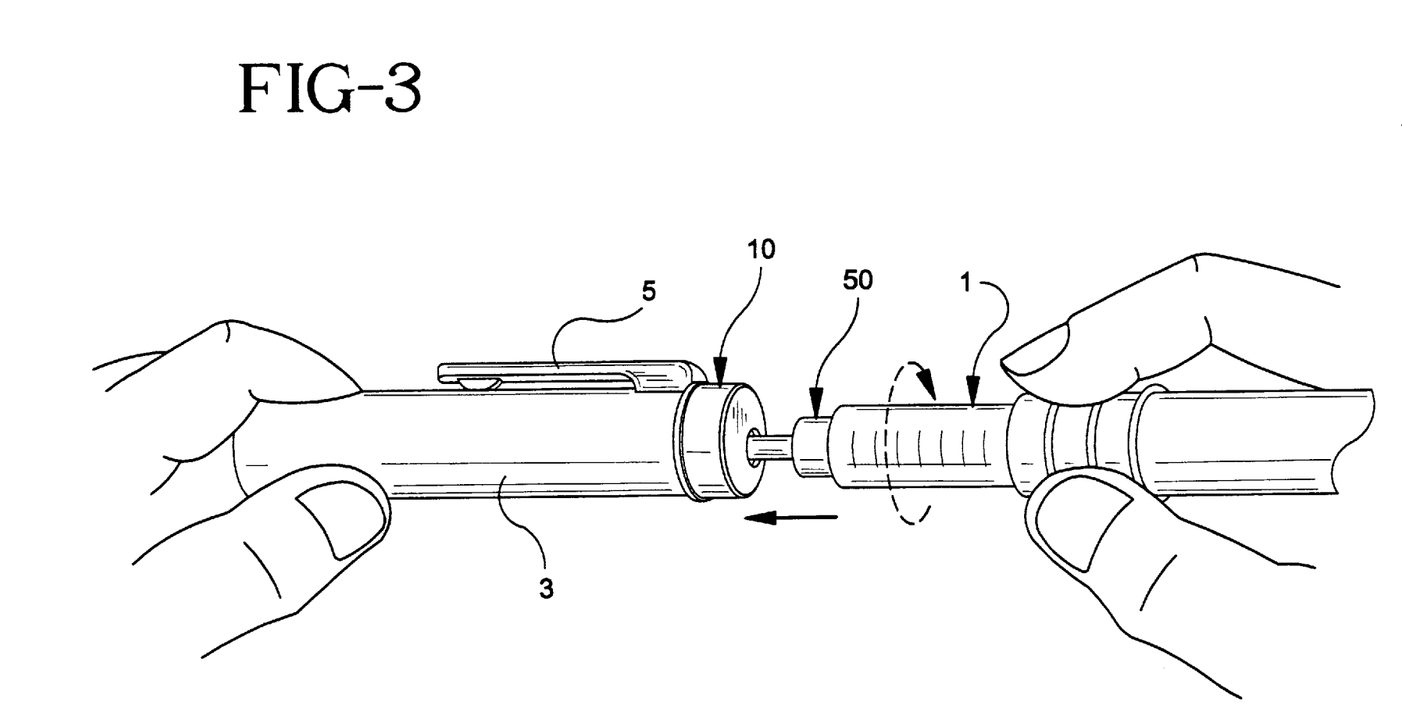
FIG. 3 is a perspective view of a pen needle according to the present invention being attached to an adaptor threaded on the distal end of a medication delivery pen.
Figure 4:
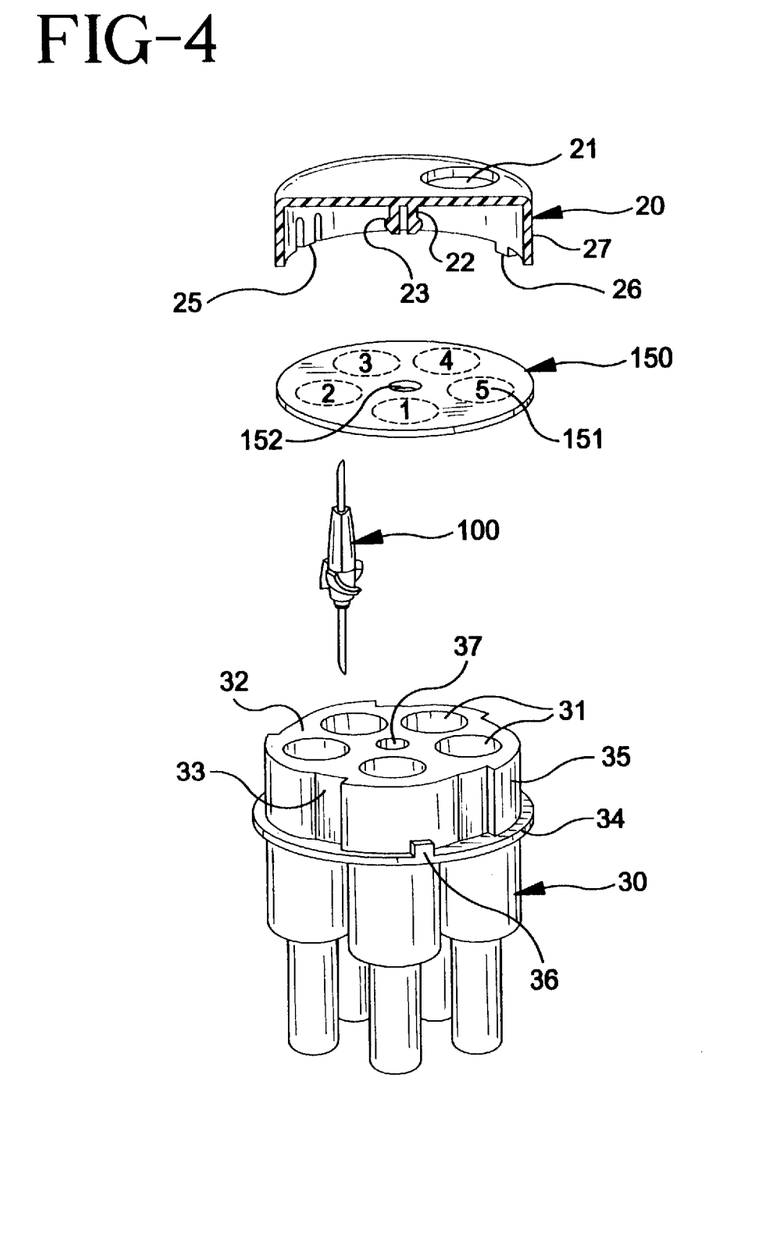
FIG. 4 is an exploded perspective view of the pen needle magazine dispenser shown in FIG. 2.

A pen needle magazine dispenser in accordance with the subject invention is identified generally by the numeral 10 in FIGS. 2, 3 and 4. FIG. 2 is an exploded perspective view of a cap 3 on a medication delivery pen 1 and a pen needle magazine dispenser 10, according to the present invention. Cap 3 includes a clip 5 and an open end 7 dimensioned to receive pen needle magazine dispenser 10. FIG. 3 is a perspective view showing the operation of inserting an adaptor 50 on distal end 6 of medication delivery pen 1 into pen needle magazine dispenser 10 and the rotational motion used to attach a pen needle assembly 100 to adaptor 50.

As shown in the exploded perspective view in FIG. 4, pen needle magazine dispenser 10 includes a cover 20 and a container 30. Container 30 includes a plurality of cavities 31 about the circumference of container 30, with each cavity 31 dimensioned to receive a pen needle assembly 100, described further below. Each pen needle assembly 100 is originally sealed in its respective cavity 31 by a disc shaped label or sterility barrier 150 that is attached to an upper surface 32 of container 30. Label 150 provides sterility for unused pen needle assemblies 100 contained in each cavity 31 and a simple means for the user to identify whether the pen needle assembly in a particular cavity has been used.

Pen needle magazine dispenser 10 is initially loaded with a predetermined number of pen needle assemblies 100 in the plurality of cavities 31, with all of the cavities 31 being sealed by sterility barrier 150 and having a number 151 thereon corresponding to each cavity 31. Each number 151 or other indicia on label 150 indicates to the user how many unused pen needle assemblies 100 remain in pen needle magazine dispenser 10. Label 150 includes a central opening 152 through which cover 20 is mounted on container 30 and is scored at the location of each cavity 31 without, of course, affecting the integrity of the seal to allow for controlled breaking when adaptor 50 on medication delivery pen 1 is pressed through label 150 when loading pen needle assembly 100 on adaptor 50. The controlled breaking of the scored area allows adaptor 50 on medication delivery pen 1 to be inserted through label 150 to mate with pen needle assembly 100 within cavity 31.

After pen needle magazine dispenser 1, shown in FIG. 4, is loaded with new needle assemblies 100 and fully assembled with cover 20 rotatably mounted on container 30 and label 150 attached to upper surface 32 over one of cavities 31, cover 20 is rotated with respect to container 30 to move slot 21 over the first loaded cavity 31. As shown in FIG. 4, container 30 includes a central opening 37 and a plurality of ratchet teeth 33 selectively spaced around an outer wall 35 of container 30. Container 30 also includes a flange 34 that extends outwardly from outer wall 35 of container 30 below ratchet teeth 33 and an end of travel lock pin 36 that extends up from flange 34. End of travel lock pin 36 works with a similar end of travel lock key 26 located on the underside of cover 20 to stop rotation of cover 20 on container 30 when all cavities have passed under slot 21.

Cover 20 includes a central post 22 having an enlarged head 23. In addition, cover 20 includes an outer lip 27 around its circumference that extends down and over container 30, when cover 20 is attached to container 30. Outer lip 27 includes a ratchet tooth 25 extending therefrom in the direction of container 30 that is dimensioned to work with the plurality of ratchet teeth 33 on container 30 to prevent cover 20 from rotating in a predetermined direction. Cover 20 is rotatably attached to container 30 after container 30 has been loaded with pen needle assemblies 100 and label 150 has been attached to upper surface 32 of container 30 by inserting central post 22 into central opening 37 in container 30 until enlarged head 23 snaps to central opening 37. When enlarged head 23 snaps into central opening 37, cover 20 is attached to container 30 such that ratchet teeth 33 on container 30 engage with ratchet tooth 25 extending from cover 20 to only permit cover 20 to rotate in one direction, i.e., a clockwise direction. Therefore, cover 20 is not permitted to rotate in the counter-clockwise direction or to move slot 21 back over cavities 31 containing used pen needles 100.

Of course, when cover 20 is attached to container 30 it is important to locate end of travel lock key 26 on cover 20 adjacent to end of travel lock pin 36 on container 30, such that cover 20 can proceed with a full clockwise rotation on container 30. Therefore, when all cavities have been accessed using slot 21 on cover 20 and cover 20 has completed a complete clockwise rotation on container 30, end of travel lock key 26 on cover 20 will again be adjacent to end of travel lock pin 36 on container 30 but now will prevent further rotation in the clockwise direction. In the current embodiment, cover 20 can never be rotated in the counter-clockwise direction on container 30 because of the above-described interaction of ratchet teeth 25 and 33.

Figure 5:
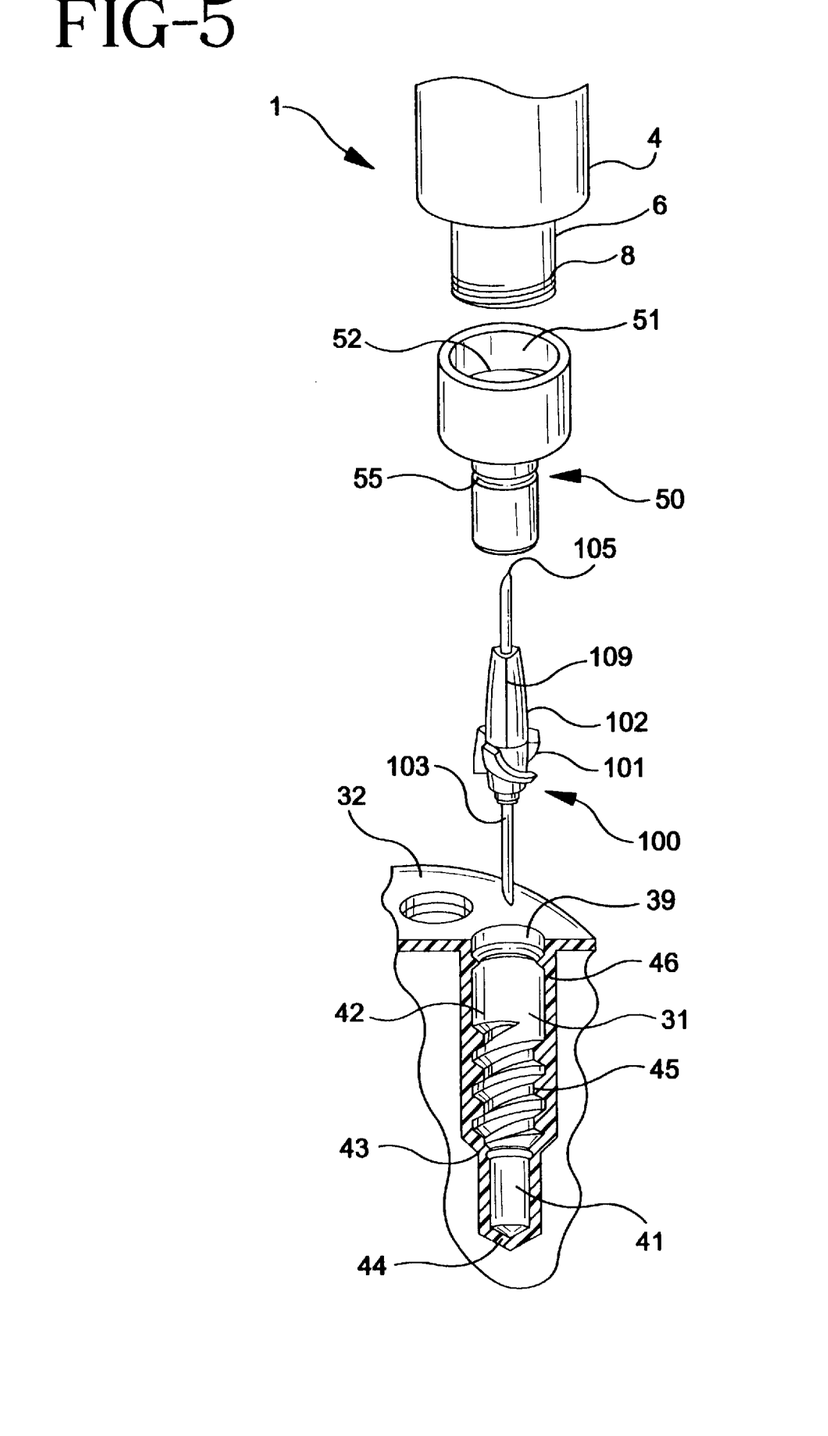
FIG. 5 is an exploded perspective view of the adaptor and pen needle with a partial cross-sectional view of the pen needle magazine dispenser.

As described above, container 30 includes a plurality of cavities 31 around its circumference that are dimensioned to receive pen needle assemblies 100, more clearly shown in FIGS. 5 and 6 and further described below. FIG. 5 shows a cross-sectional view of one of said plurality of cavities 31 and FIG. 6 more clearly shows adaptor 50. As shown in FIG. 5, each cavity 31 includes an open end 39 leading to an upper section 42 and a bottom section 41 leading to a closed end 44. Upper section 42 includes a retaining ring 46 that mates with a matching retaining ring 55 on adaptor 50, when adaptor 50 is inserted into cavity 31 to attach or detach pen needle assembly 100 to adaptor 50. Bottom section 41 has a smaller diameter than upper section 42 with a shelf 43 formed where sections 41 and 42 meet. A set of threads 45 are located in the bottom part of upper section 42 adjacent to shelf 43 and bottom section 41 is dimensioned to receive a distal point 104 on pen needle assembly 100.

Figure 6:
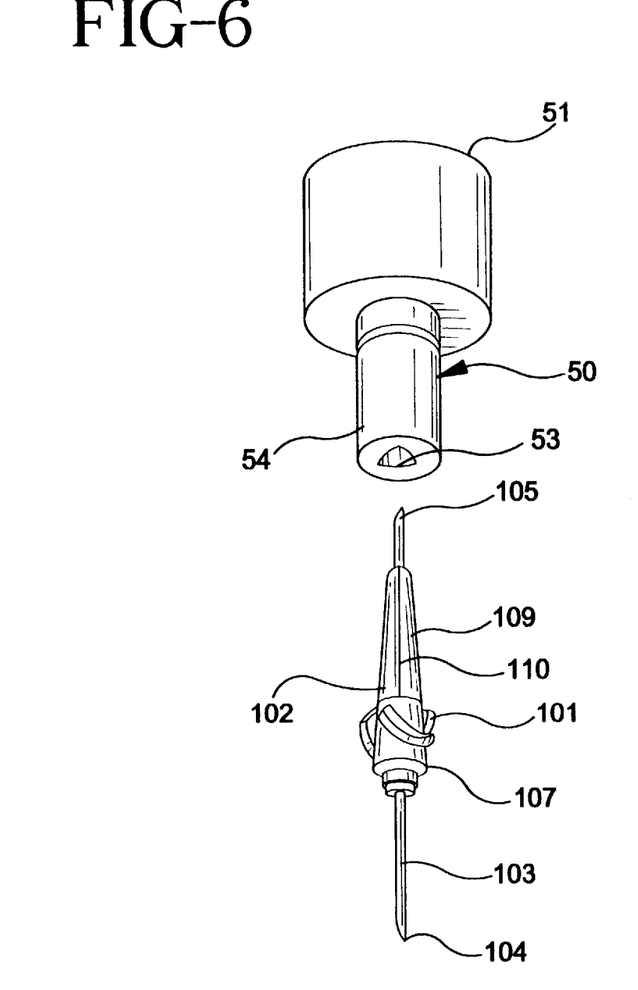
FIG. 6 is another exploded view of the adaptor and pen needle according to the present invention.

As shown in FIGS. 5 and 6, pen needle assembly 100 includes a hub 102 having a triangular shaped proximal end 109 and a distal end 107 having a set of threads 101 thereon dimensioned to mate with the set of threads 45 within cavities 31. A needle cannula 103 is mounted within hub 102 and includes a distal point 104 and a proximal point 105, wherein proximal point 105 extends from triangular shaped proximal end 109 and distal point 104 extends out of distal end 107 on hub 102. Proximal end 109 also includes one or more splines 110 to improve the rotational operation of hub 102 within cavity 31 and increase the force-fit between hub 102 and adaptor 50. After a plurality of pen needle assemblies 100 have been loaded into pen needle magazine dispenser 10 and assembled, as shown in FIG. 4, pen needle magazine dispenser 10 is ready for mounting in opening 7 of cap 3, as shown in FIG. 2.

As shown in FIG. 3, each newly designed pen needle assembly 100 within cavity 31 can only be removed and mounted on a medication delivery pen having an adaptor 50 according to the present invention. As shown in FIG. 5, adaptor 50 includes an open proximal end 51 having a set of threads 52 dimensioned to mate with threads 8 on distal end 6 of conventional medication delivery pen 1. Adaptor 50 also includes a unique triangular shaped opening 53 in its distal end 54. After adaptor 50 has been threaded onto distal end 6 of pen 1, distal end 54 of adaptor 50 is used to remove pen needle assembly 100 from cavity 31 by inserting triangular shaped proximal end 109 of needle assembly 100 into triangular shaped opening 53 in adaptor 50. When triangular shaped proximal end 109 of needle assembly 100 is inserted into triangular shaped opening 53 in adaptor 50, rotation of medication delivery pen 1 causes pen needle assembly 100 to rotate within cavity 31 and drive triangular shaped proximal end 109 of needle assembly 100 into a forced fit with triangular shaped opening 53 in adaptor 50.

As pen 1 is rotated and needle assembly 100 is driven into adaptor 50, proximal point 105 of pen needle assembly 100 pierces rubber septum 2 of the cartridge in pen 1 to place needle cannula 103 in communication with medication contained within the cartridge in pen 1. The forced fit also holds proximal point 105 within rubber septum 2 and needle assembly 100 within adaptor 50 during the injection of medication from the cartridge in pen 1.

After use, the used pen needle assembly 100 mounted on adaptor 50 on medication delivery pen 1 is reinserted into cavity 31 until retaining rings 46 and 55 mate and the set of threads 101 on pen needle assembly 100 come into contact with the set of threads 45 within cavity 31. Medication delivery pen 1 is then rotated in the opposite direction to thread pen needle assembly 100 back into cavity 31 and pen 1 is then pulled out of container 30 as pen needle assembly 100 is pulled out adaptor 50.

The user then rotates cover 20 until slot 21 is aligned with the next cavity 31 having an unused pen needle 100 that is still covered by label 150. As cover 20 is rotated ratchet tooth 25 travels over one set of ratchet teeth 33 on container 30, which then prevents cover 20 from rotating in the opposite direction. Of course, an alternative to the unidirectional cover shown in the drawings and described above would be a design that allows the user to rotate slot 21 back to previously used needles. In that case, no ratchet mechanism would be needed but the other features of the present invention could still be used in such a device. However, as described above and shown in the drawings, the current design allows the user to repeatedly rotate cover 20 to each cavity 31 until all of the pen needle assemblies 100 have been used and the last cavity 31 has been encountered by slot 21 on cover 20. That last cavity could be left empty so that the user will know that all pen needle assemblies 100 have been used and thereby indicate that pen needle magazine dispenser 10 should now be properly disposed of. In addition, by providing an empty cavity 31 with all filled cavities 31 being fully enclosed behind cover 20, all the used pen needle assemblies 100 and their proximal points 105 would be protected from accidental needle sticks, since cover 20 would no longer be able to rotate in either direction. As explained above, further rotation would be prevented by interaction between end of travel lock pin 36 on container 30 and end of travel lock key 26 on cover 20. If it is desired to use all the cavities 31 in container 30 to hold pen needle assemblies 100, the apparatus of the present invention can have a final rotational movement that is limted to a one-half (½) unit turn. In that case, slot 21 would be finally positioned between the first cavity and the last cavity with all pen needle assemblies 100 being covered and contained within container 30 and cover 20 being prevented from rotation in either direction.

While the invention has been described with respect to a preferred embodiment, it is apparent that various changes can be made without departing from the scope of the invention as defined by the appended claims. For example, adaptor 50 can be integrally molded onto or permanently attached to distal end 6 of a medication delivery pen 1 rather than being a separate part.

What is claimed is:

1. An apparatus for storing and dispensing a plurality of needle assemblies for use on a medication delivery pen having a removable cap, said apparatus comprising:

a container having an upper surface including a plurality of cavities with each cavity being dimensioned to receive a needle assembly;

means for attaching said container on a medication delivery pen; and a cover rotatably mounted on said container, said cover having a slot that can be rotated into alignment with one of said plurality of cavities in said container to provide access through said cover to a needle assembly located in said one of said plurality of cavities.

2. An apparatus according to claim 1, wherein said means for attaching said container to the medication delivery pen comprises means for mounting said container within an open end of a removable cap on the medication delivery pen.

3. An apparatus according to claim 1, further comprising means for preventing said cover from rotating on said container in a reverse direction while permitting said cover to rotate on said container in a forward direction to rotate said slot into alignment with one of said plurality of cavities in said container.

4. An apparatus according to claim 3, wherein said means for preventing rotation of said cover in said reverse direction includes a ratchet tooth on said cover that interacts with a plurality of ratchet teeth on said container to prevent said cover from rotating on said container in said reverse direction after said slot is aligned with one of said plurality of cavities.

5. An apparatus according to claim 3, further comprising means for preventing said cover from further rotation in said forward direction after said slot has been rotated into alignment with each of said plurality of cavities in said container.

6. An apparatus according to claim 5, wherein said means for preventing said cover from further rotation in said forward direction includes an end of travel lock key on an inside surface of said cover that interacts with an end of travel lock pin on said upper surface of said container.

7. An apparatus according to claim 1, further comprising a sterility barrier over each of said plurality of cavities.

8. An apparatus according to claim 7, wherein each of said sterility barrier includes an indicia that identifies the number of unused needle assemblies remaining in the apparatus.

9. An apparatus according to claim 8, wherein said sterility barrier includes scoring over each of said plurality of cavities to permit said sterility barrier to be pierced by the medication delivery pen accessing said cavity behind said scoring.

10. An apparatus according to claim 1, further comprising means for attaching one of said needle assemblies onto the medication delivery pen.

11. An apparatus according to claim 10, wherein said attaching means includes an adaptor having a set of threads that mate with a set of threads on a distal end of the medication delivery pen to attach said adaptor to the medication delivery pen.

12. An apparatus according to claim 11, wherein said attaching means further includes a set of threads within each of said cavities that mate with a set of threads on said needle assembly to cause said needle assembly to attach to said adaptor when the medication delivery pen is rotated in a first direction and to release from said adaptor when the medication delivery pen is rotated in a second direction.

13. An apparatus for storing and dispensing a plurality of needle assemblies for use on a medication delivery pen, said apparatus comprising:

a container having an upper surface including a plurality of cavities with each cavity being dimensioned to receive a needle assembly;

means for attaching a needle assembly from one of said plurality of cavities onto the medication delivery pen; and a cover rotatably mounted on said container, said cover having a slot that can be rotated into alignment with one of said plurality of cavities in said container to provide access through said cover to a needle assembly located in said one of said plurality of cavities.

14. An apparatus according to claim 13, wherein said attaching means includes an adaptor having a set of threads that mate with a set of threads on a distal end of the medication delivery pen to attach said adaptor to the medication delivery pen.

15. An apparatus according to claim 14, wherein said attaching means further includes a set of threads within each of said cavities that mate with a set of threads on said needle assembly to cause said needle assembly to attach to said adaptor when the medication delivery pen is rotated in a first direction and to release from said adaptor when the medication delivery pen is rotated in a second direction.

* * * * *